United States Patent
Shi et al.

(10) Patent No.: US 6,893,884 B2
(45) Date of Patent: May 17, 2005

(54) METHOD AND APPARATUS FOR MEASURING DOPANT PROFILE OF A SEMICONDUCTOR

(75) Inventors: Li Shi, Austin, TX (US); Uttam Shyamalindu Ghoshal, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 383 days.

(21) Appl. No.: 10/112,482

(22) Filed: Mar. 28, 2002

(65) Prior Publication Data

US 2003/0186471 A1 Oct. 2, 2003

(51) Int. Cl.[7] ............................................. H01L 21/66
(52) U.S. Cl. ........................... 438/17; 438/14; 324/765; 324/769
(58) Field of Search ................ 324/765–769; 438/14–18

(56) References Cited

U.S. PATENT DOCUMENTS 6,171,959 B1 * 1/2001 Nagabushnam ............. 438/683
6,467,951 B1 * 10/2002 Ghoshal ...................... 374/45

OTHER PUBLICATIONS

Williams et al., "Microscopy of Chemical–Potential Variations on an Atomic Scale", Nature, vol. 344, p. 317–319 (1990).*

* cited by examiner

Primary Examiner—Asok Kumar Sarkar
(74) Attorney, Agent, or Firm—Casimer K. Salys; Dillon & Yudell LLP

(57) ABSTRACT

A method and apparatus for measuring dopant profile of a semiconductor is disclosed. Initially, the temperature of a tip of a probe and the temperature of a semiconductor sample are ascertained. Then, a voltage at a location on a surface of the semiconductor sample is obtained via the tip of the probe. The dopant concentration at the location of the surface of the semiconductor sample is subsequently determined by combining the obtained voltage and the temperature difference between the probe tip and the semiconductor sample. The above-mentioned steps can be repeated in order to generate a dopant profile of the semiconductor.

11 Claims, 2 Drawing Sheets

METHOD AND APPARATUS FOR MEASURING DOPANT PROFILE OF A SEMICONDUCTOR

BACKGROUND OF THE INVENTION

1. Technical Field

The present invention relates to semiconductor characterization in general, and in particular to a method and apparatus for measuring the dopant profile of a semiconductor. Still more particularly, the present invention relates to a method and apparatus for measuring a two-dimensional dopant profile of a semiconductor.

2. Description of the Prior Art

Present-day integrated circuit manufacturing technology demands accurate knowledge of the concentration of dopants that have been incorporated into substrates. This is because dopant concentration within a substrate has a significant effect on the performance of discrete devices, such as transistors, that are built on the substrate. In addition, it is also important to have the knowledge of the dopant concentration in a spatial extent for process development.

Typically, the active region of a field-effect transistor (FET) is engineered by incorporating dopants, such as arsenic, boron, or phosphorate, in a concentration ranging from $10^{15}$ cm$^{-3}$ to $10^{20}$ cm$^{-3}$. When building FETs at a submicron level, it is necessary to quantify the variation of the above-mentioned dopants at the junction regions of submicron FETs to a resolution of 10 nm or less over four orders of magnitude in dopant concentration.

There are several prior art techniques for measuring dopant profiles of a semiconductor, which include Scanning Capacitance Microcopy, Scanning Kelvin Probe Microscopy, Scanning Preading Resistance Microscopy, etc. However, all of the prior art techniques generally do not have a very high sensitivity and/or spatial resolution to meet the demands of integrated circuit manufacturing at submicron levels. Furthermore, the sensitivity of some of the prior art techniques tends to decrease as the spatial resolution increases with the usage of sharper probes. Consequently, it would be desirable to provide an improved method and apparatus for measuring dopant profile of a semiconductor.

SUMMARY OF THE INVENTION

In accordance with a preferred embodiment of the present invention, the temperature of a tip of a probe and the temperature of a semiconductor sample are ascertained. A voltage at a location on a surface of the semiconductor sample is obtained via the tip of the probe. The dopant concentration at the location of the surface of the semiconductor sample is then determined by combining the obtained voltage and the temperature difference between the probe tip and the semiconductor sample. The above-mentioned steps can be repeated in order to generate a dopant profile of the semiconductor.

All objects, features, and advantages of the present invention will become apparent in the following detailed written description.

BRIEF DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein.

DETAILED DESCRIPTION OF A PREFERRED EMBODIMENT

The Seebeck coefficient of a semiconductor depends on the concentration of dopants within the semiconductor. For example, the Seebeck coefficient S of an n-type silicon is $$S = \frac{1}{-eT}(E_C - E_F + 2k_B T)$$

$$\approx -\frac{k_B}{e} \ln \frac{n}{N_c}$$

where e=charge

T=temperature n=dopant concentration $E_C$=conduction band energy $E_F$=Fermi energy $k_B$=Boltzman constant $N_c$=constant Thus, the dopant concentration of a semiconductor can be determined by measuring the Seebeck coefficient of the semiconductor via $$n = N_c \exp\left[-\frac{eS}{k_B}\right]$$

The Seebeck coefficient can be measured by using Scanning Thermoelectric Microscopy (STEM), as detailed in Ghoshal, Miner and Majumdar, *Proc. 19$^{th}$, Int. Thermoelectrics Conference*, p. 221 (2000), the pertinent of which is incorporated herein by reference, or Scanning Chemical Potential Microscopy (SCPM), as detailed in *Williams and Wickramasinghe, Nature*, 344, p. 317 (1990), the pertinent of which is incorporated herein by reference.

Figure 1:
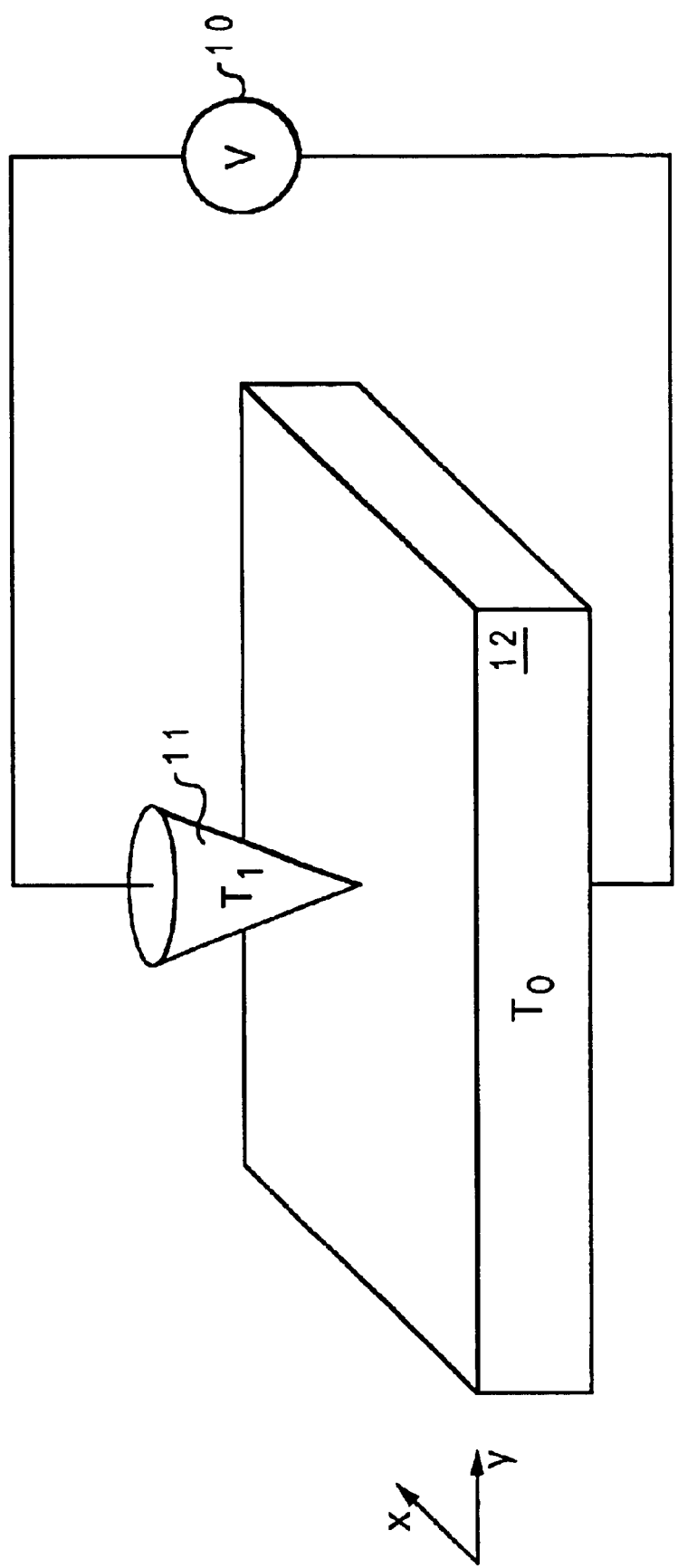
FIG. 1 is a diagram of an apparatus for measuring dopant profile of a semiconductor, in accordance with a preferred embodiment of the present invention.

Referring now to the drawings and in particular to FIG. 1, there is depicted a diagram of an apparatus for measuring dopant profile of a semiconductor, in accordance with a preferred embodiment of the present invention. As shown, a silicon sample 12 at temperature $T_0$ is scanned by a sharp metal probe 11 at temperature $T_1$. During scanning, the tip-sample gap (i.e., the gap between the tip of metal probe 11 and silicon sample 12) is regulated by an electron tunneling feedback loop of a Scanning Tunneling Microscope (STM) (not shown). The temperature at the tip-sample junction is at an intermediate temperature $T_j$ that lies between $T_1$ and $T_0$. Ignoring any small thermoelectric voltage developed in metal probe 11, the measured thermoelectric voltage by a voltmeter 10 at a point (x, y) on the surface of silicon sample 12 is $$V(x, y) = \int_\infty^0 S(\vec{r}) \nabla T(\vec{r}) \cdot d\vec{r}$$

where r=distance on silicon sample 12 from the tip of metal probe 11.

Most temperature change occurs within a few factor, m, of tip radius $r_t$ from the tip-sample junction. The dopant concentration and, thus, Seebeck coefficient S is assumed to be constant within $mr_t$ from the tip-sample junction of silicon sample 12. Hence, $$V(x, y) \approx S(x, y)(T_j - T_0)$$
$$= S(x, y)\beta(T_1 - T_0)$$

where $T_0$ temperature of silicon sample
$T_1$=temperature of metal probe tip
$T_j$=temperature of tip-sample junction
$\beta$=a constant depending on the thermal property of metal probe and silicon sample, the radius of metal probe tip, tip-sample junction, etc.

Thus, the Seebeck coefficient at a point (x,y) on the surface of silicon sample 12 can be found by:

$$S(x, y) = \frac{V(x, y)}{\beta(T_1 - T_0)}$$

By substituting S(x,y) into the above-mentioned dopant concentration equation, the dopant concentration n at a point (x,y) on the surface of silicon sample 12 can be found by:

$$n(x, y) = N_c \exp\left[-\frac{eV(x, y)}{\beta k_B(T_1 - T_0)}\right]$$

Accordingly, dopant profile of silicon sample 12 can be obtained by continuously measuring the voltage at various points (x,y) on the surface of silicon sample 12.

When using an atomically sharp etched tungsten tip having a tip radius of approximately 1 nm, and if factor m is less than 5, then the spatial resolution of the method of the present invention equals $mr_t$<10 nm. The sensitivity (or concentration resolution) of the method of the present invention can be shown as $$\frac{\delta n}{n} = \delta(\ln n)$$
$$= \frac{e}{k_B}\delta S$$
$$= \frac{e}{k_B(T_j - T_0)}(\delta V + S\delta(T_j - T_0)) \leq 4\%$$

with a temperature difference $(T_j - T_0)$=30° K, and voltage $\delta V$=1 $\mu V$, and temperature measurement resolution $\delta(T_j - T_0)$=0.1° K. Furthermore, the measured voltage signal does not decrease with tip radius; thus, the method of the present invention is free from the trade-off between sensitivity and spatial resolution, which occurs in other dopant profiling techniques such as Scanning Kelvin Force Probe Microscopy or Scanning Capacitance Microscopy.

Figure 2:
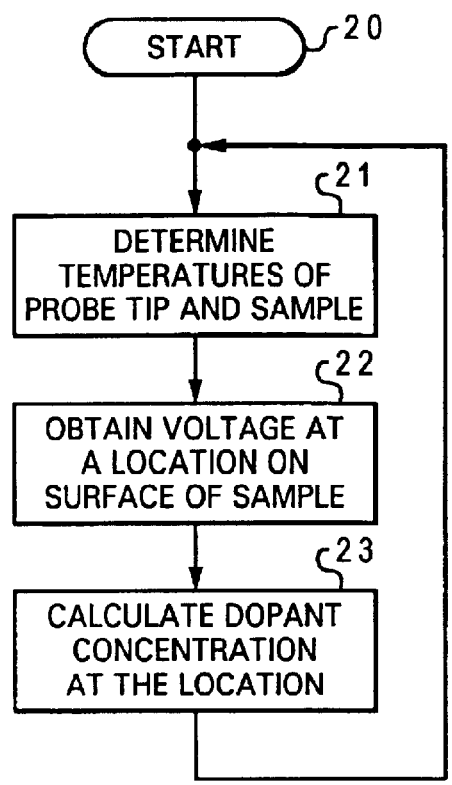
FIG. 2 is a high-level logic flow diagram of a method for measuring dopant profile of a semiconductor, in accordance with a preferred embodiment of the present invention.

With reference now to FIG. 2, there is depicted a high-level logic flow diagram of a method for measuring a two-dimensional dopant profile of a semiconductor, in accordance with a preferred embodiment of the present invention. Starting at block 20, the temperatures of a probe tip and a semiconductor sample are initially determined, as shown in block 21. For example, the probe can be at ambient temperature that can be measured by a thermometer, and the semiconductor sample can be at a higher temperature than the probe, which can be measured by a thermocouple that is well-known to those skilled in the art. Then, the voltage at a location on the surface of the semiconductor sample is obtained via the tip of the probe, as depicted in block 22. The dopant concentration of the semiconductor sample at that location can be calculated by combining the determined voltage and temperature difference between the probe tip and the semiconductor sample, as shown in block 23. A dopant profile can be generated by repeating the steps depicted in block 21 through block 23, which is to measure the voltage at various locations on the surface of the semiconductor sample.

The knowledge of junction geometries are critical for the design of field-effect transistors (FETs) having a channel length of less than 100 nm. The method of the present invention is particularly useful in determining the boundaries of shallow source and drain junctions, and the profiles near the channel surface of a FET.

Figure 3:
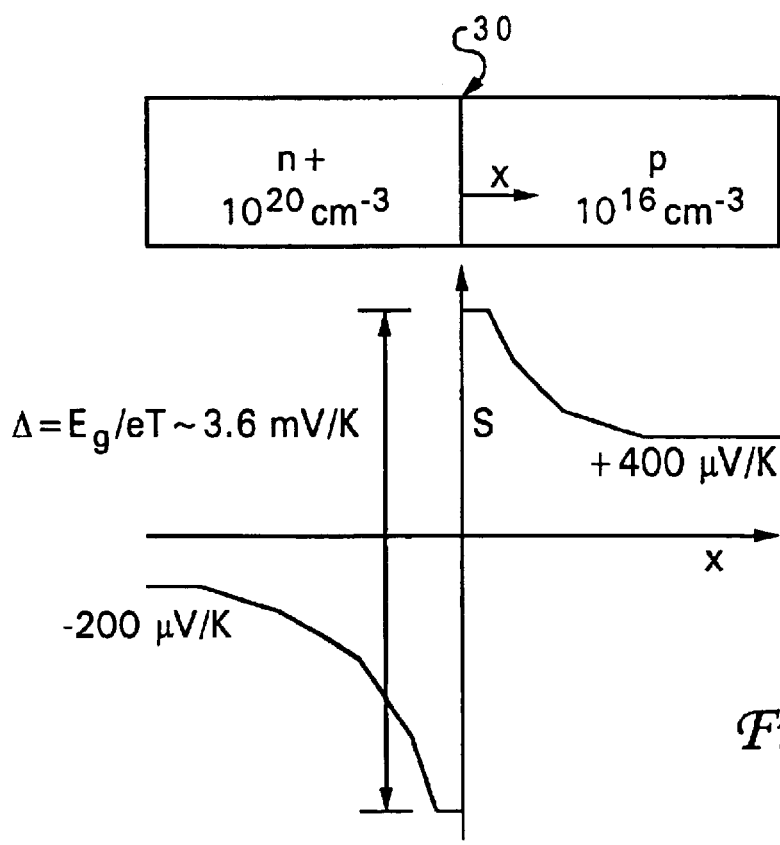
FIG. 3 is a graph of Seebeck coefficient verses channel location at a p-n junction of a semiconductor.

Referring now to FIG. 3, there is illustrated a graph of Seebeck coefficient verses channel location at a p-n junction of a semiconductor. As shown, the Seebeck coefficient profile is discontinuous at a p-n junction 30. There is also a sign change at p-n junction 30. The discontinuity is directly related to the band gap of the semiconductor and the local temperature ($\Delta$=$E_g$/eT). For silicon, $E_g$=1.1 eV, so that $\Delta$=3.6 mV/° K. The magnitude of $\Delta$ is large so that the boundaries can be determined accurately.

As has been described, the present invention provides a method and apparatus for measuring a two-dimensional dopant profile of a semiconductor. Although only an n-type silicon is used to illustrate the present invention, it is understood by those skilled in the art that the principle of the present invention can also be applied to p-type silicon or other types of substrates. For example, the present invention is applicable to Germanium substrates and Gallium Arsenide substrates.

The present invention takes advantage of the strong dependance of Seebeck coefficient of a semiconductor on its doping concentration. As such, the dopant profile can be obtained by measuring the Seebeck coefficient variations via Scanning Thermoelectric Microscopy or Scanning Chemical Potential Microscopy. The advantages of the method and apparatus of the present invention include superior spatial resolution (better than 10 nm) and better sensitivity (higher than 4%).

While the invention has been particularly shown and described with reference to a preferred embodiment, it will be understood by those skilled in the art that various changes in form and detail may be made therein without departing from the spirit and scope of the invention.

What is claimed is:

1. A method for measuring dopant concentration of a semiconductor, said method comprising:

determining temperature of a tip of a probe;
   determining temperature of a semiconductor sample;
   determining a voltage at a location on a surface of said semiconductor sample with said tip of said probe; and
   determining dopant concentration at said location of said surface of said semiconductor sample by $$n(x, y) = N_c \exp\left[-\frac{eV(x, y)}{\beta k_B(T_1 - T_0)}\right]$$

where n(x,y)=dopant concentration at location (x,y) on said semiconductor sample surface
e=charge of electron V(x,y)=voltage at location (x,y) on said semiconductor sample surface $T_0$=temperature of said semiconductor sample $T_1$=temperature of said tip of said probe $K_B$=Boltzman constant $\beta$=constant $N_c$=constant.

2. The method of claim 1, wherein said tip of said probe is controlled by an electron tunneling feedback loop of a Scanning Tunneling Microscope.

3. The method of claim 1, wherein said method further includes a step of repeating said determining steps to generate a dopant profile of said semiconductor sample.

4. The method of claim 1, wherein said semiconductor sample is a silicon substrate.

5. The method of claim 1, wherein said semiconductor sample is a germanium substrate.

6. The method of claim 1, wherein said semiconductor sample is a gallium arsenide substrate.

7. An apparatus for measuring dopant concentration of a semiconductor, said apparatus comprising:

means for determining temperature of a tip of a probe;

means for determining temperature of a semiconductor sample;

means for determining a voltage at a location on a surface of said semiconductor sample with said tip of said probe; and means for determining dopant concentration at said location of said surface of said semiconductor sample by $$n(x, y) = N_c \exp\left[-\frac{eV(x, y)}{\beta k_B (T_1 - T_0)}\right]$$

where n(x,y)=dopant concentration at location (x,y) on said semiconductor sample surface e=charge of electron V(x,y)=voltage at location (x,y) on said semiconductor sample surface $T_0$=temperature of said semiconductor sample $T_1$=temperature of said tip of said probe $K_B$=Boltzman constant $\beta$=constant $N_c$=constant.

8. The apparatus of claim 7, wherein said tip of said probe is controlled by an electron tunneling feedback loop of a Scanning Tunneling Microscope.

9. The apparatus of claim 7, wherein said semiconductor sample is a silicon substrate.

10. The apparatus of claim 7, wherein said semiconductor sample is a germanium substrate.

11. The apparatus of claim 7, wherein said semiconductor sample is a gallium arsenide substrate.

* * * * *